United States Patent
De La Poterie et al.

(10) Patent No.: US 6,235,293 B1
(45) Date of Patent: May 22, 2001

(54) COSMETIC COMPOSITIONS COMPRISING A FILM-FORMING POLYMER AND A PROCESS THEREOF

(75) Inventors: Valérie De La Poterie, Le Chatelet en Brie; Isabelle Bara, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/066,889

(22) Filed: Apr. 28, 1998

(30) Foreign Application Priority Data

Apr. 28, 1997 (FR) .................................. 97 05224

(51) Int. Cl.⁷ .............................. A61K 6/00; A61K 7/00; A61K 7/025
(52) U.S. Cl. ............................. 424/401; 424/64
(58) Field of Search ..................... 424/64, 401, 78.03; 514/844, 845

(56) References Cited

U.S. PATENT DOCUMENTS

| | | | |
|---|---|---|---|
| 3,928,261 | 12/1975 | Ashidaga et al. | 260/899 |
| 4,423,031 | * 12/1983 | Murui et al. | 424/63 |
| 4,795,631 | 1/1989 | Sheehan | 424/64 |
| 5,238,678 | 8/1993 | Shiozawa et al. | 424/63 |
| 5,538,717 | 7/1996 | La Poterie | 424/61 |
| 5,601,808 | 2/1997 | Mellul et al. | 424/61 |

FOREIGN PATENT DOCUMENTS

| | | |
|---|---|---|
| 0 206 671 A2 | 12/1986 | (EP) . |
| 0 206 671 A3 | 12/1986 | (EP) . |
| 0 568 035 | 11/1993 | (EP) . |
| 0 648 485 | 4/1995 | (EP) . |
| 0 658 609 | 6/1995 | (EP) . |
| 0 673 612 | 9/1995 | (EP) . |
| 0 680 742 | 11/1995 | (EP) . |
| 0 749 747 | 12/1996 | (EP) . |
| 0 775 483 | 5/1997 | (EP) . |
| 0 793 957 | 9/1997 | (EP) . |
| 1 501 403 | 11/1967 | (FR) . |
| 2 175 332 | 10/1973 | (FR) . |
| 2 229 393 | 12/1974 | (FR) . |
| 2 540 131 | 8/1984 | (FR) . |
| 2 679 769 | 2/1993 | (FR) . |
| 2 705 876 | 12/1994 | (FR) . |
| 2 715 916 | 8/1995 | (FR) . |
| 2 721 824 | 1/1996 | (FR) . |
| 2 727 608 | 6/1996 | (FR) . |
| 2 727 909 | 6/1996 | (FR) . |
| 2 745 272 | 8/1997 | (FR) . |
| WO 96/36310 | 11/1996 | (WO) . |
| WO 97/01321 | 1/1997 | (WO) . |

OTHER PUBLICATIONS

English Language Derwent Abstract of FR 2 721 824.
English Language Derwent Abstract of FR 2 727 608.
English Language Derwent Abstract of FR 2 727 909.
English Language Derwent Abstract of FR 2 745 272.
English Language Derwent Abstract of EP 0 793957.
English Language Derwent Abstract of EP 0 775 483.
English Language Derwent Abstract of EP 0 749 747.
Patent Abstracts of Japan, Publication No. JP 5070321, Publication Date Mar. 23, 1993.
English Language Derwent Abstract of JP 54049338.
English Language Derwent Abstract of EP 0 658 609.
English Language Derwent Abstract of EP 0 673 612.
English Language Derwent Abstract of FR 2 175 332.
English Language Derwent Abstract of FR 2 540 131.
English Language Derwent Abstract of FR 2 705 876.
English Language Derwent Abstract of FR 2 715 916.

* cited by examiner

Primary Examiner—Thurman K. Page
Assistant Examiner—S. Howard
(74) Attorney, Agent, or Firm—Finnegan, Henderson, Farabow, Garrett & Dunner, L.L.P.

(57) ABSTRACT

Composition for the skin, semi-mucous membranes and/or mucous membranes, comprising a polymer system capable of forming a film having a hardness of less than 50; and a make-up process and a non-therapeutic treatment process for the skin, semi-mucous membranes and/or mucous membranes, comprising applying a composition according to the invention thereto.

64 Claims, No Drawings

COSMETIC COMPOSITIONS COMPRISING A FILM-FORMING POLYMER AND A PROCESS THEREOF

Applicants reference herein the patent applications of VALÉRIE DE LA POTERIE and JEAN-LOUIS H. GUERET for FILM-FORMING POLYMER-BASED COSMETIC COMPOSITION AND PRODUCT FOR THE LIPS, and of VALÉRIE DE LA POTERIE for COMPOSITIONS COMPRISING A POLYMERIC SYSTEM COMPRISING AT LEAST ONE FLUORINATED POLYMER IN DISPERSION, AND USES THEREOF, filed on even date herewith and incorporate the disclosures thereof specifically by reference herein.

The present invention relates to compositions, in particular cosmetic compositions, which can be applied to the skin, semi-mucous membranes and/or mucous membranes. The compositions in particular comprise a polymer system and can be used as a make-up product.

Compositions to be applied to the skin, to semi-mucous membranes and/or to mucous membranes, such as lipsticks and foundations, are generally in the form of sticks, supple pastes or cast pastes and include fatty substances such as oils, pasty compounds and/or waxes, and a particular phase generally composed of fillers and pigments.

However, when they are applied to the support, these compositions have the drawback of transferring. This is understood to mean that the composition is liable to become deposited, at least partly, onto certain supports with which it is placed in contact, such as, for example, a glass, a cup, clothing or the skin. On becoming deposited, the composition leaves a trace on the support. This thus results in mediocre persistence of the composition on the skin, the semi-mucous membranes or the mucous membranes, and makes repeated application of the composition at regular intervals necessary.

Moreover, the appearance of unacceptable traces on certain items of clothing, and in particular on the collars of shirts, may put certain consumers off using this type of make-up.

Another drawback of these compositions lies in the problem of migration, since it has been observed that certain compositions have a tendency to travel in the wrinkles and/or fine lines in the skin, in the case of foundations; in the fine lines around the lips, in the case of lipsticks; and in the folds of the eyelids, in the case of eyeshadows. It has also been observed, especially in the case of eyeshadows, that lines appear in the make-up, these lines being generated by the movements of the eyelids. It has also been observed that eyeliners can also run. All of these phenomena give rise to an aesthetically unpleasant effect which it would obviously be desirable to avoid.

Many cosmeticians have for several years been interested in "transfer-free" cosmetic compositions, which transfer only a little or not at all, especially transfer-free lipsticks or foundations. Thus, transfer-free lipstick compositions containing from 1 to 70% by weight of liquid silicone resin containing repeating silicate units, from 10 to 98% by weight of a volatile silicone oil and pulverulent fillers have been envisaged. However, the film obtained on the lips after the silicone oil has evaporated has the drawback of becoming uncomfortable over time (sensation of dryness and tautness).

Transfer-free lipsticks containing a volatile silicone and a silicone resin containing an esterified pendant chain having at least 12 carbon atoms are also known. The film of lipstick especially has the drawback of lacking in comfort once it has been applied, in particular of being too dry.

There is thus still a need for a cosmetic composition which transfers little or not at all, i.e. a "transfer-free" composition, while at the same time having good cosmetic properties, and in particular allowing a flexible and homogeneous film to be obtained.

The aim of the present invention is to propose a composition which makes it possible to obtain a film with very good staying power, which does not transfer and does not mark a support with which it might come into contact, and which does not migrate over time.

Thus, one subject of the invention is a composition which can be applied to a support selected from the skin, semi-mucous membranes and/or mucous membranes, in particular a lip stick composition, comprising a polymer system comprising at least one film-forming radical polymer, the polymer system (or the film formed therefrom) having a glass transition temperature (Tg) less than or equal to 10° C. and a minimum film-forming temperature (MFT) less than or equal to 15° C., the polymer system being capable of forming a film having a hardness of less than or equal to 50.

Another subject of the invention is a lip composition containing a polymer composition capable of forming a film on the lips and of following the movements of the lips, the polymer system comprising a radical film-forming polymer obtained from the copolymerization of $C_1$–$C_8$ alkyl methacrylate monomers, optionally combined with acrylic acid, styrene and α-methylstyrene.

Another subject of the invention is a non-therapeutic treatment or make-up process for a support selected from the skin, semi-mucous membranes and/or mucous membranes, in particular the lips of the face, this process consisting in applying a polymer system or a composition comprising it, as defined above, to the support.

Another subject is the use, for the manufacture of a composition intended for therapeutically treating the skin, semi-mucous membranes and/or mucous membranes, in particular the lips of the face, of the polymer system or of a composition comprising it.

Another subject is the use, in a composition which can be applied to the skin, semi-mucous membranes and/or mucous membranes, of the polymer system in order to reduce the transfer and/or migration of the composition.

It has been observed that the composition according to the invention can be applied easily and can spread easily and uniformly on the skin, semi-mucous membranes and mucous membranes, in particular the lips of the face.

The composition according to the invention especially finds a particularly advantageous application in the field of making up and/or care for the skin, mucous membranes and/or semi-mucous membranes. The term mucous membrane is understood to refer in particular to the inner part of the lower eyelid; the term semi-mucous membranes is understood to refer more particularly to the lips of the face.

The composition according to the invention can provide a homogeneous film which has a light texture and remains comfortable to wear throughout the day. The film is soft, supple, elastic and flexible on the skin, while at the same time retaining good cohesion; it follows the movements of the support on which it is deposited, without cracking and/or becoming detached. In particular, it adheres perfectly to the lips of the face. Thus, the film obtained after application of the composition to the support is capable of showing good staying power on this support. The composition according to the invention is also suitable for making up the body. The composition according to the invention can be applied most particularly in the field of make-up products for the lips of the face, in particular as a lip composition, preferably a lipstick. It also finds another advantageous application in the field of eyeliners.

Moreover, the film obtained can be very shiny, or more or less matte, depending on the nature of the constituents in the composition, resulting in a wider range of shiny or matte make-up products to choose from.

The composition according to the invention thus comprises a polymer system which comprises at least one radical-type synthetic film-forming polymer. The term radical polymer is understood to refer to a polymer obtained by polymerization of monomers containing unsaturation, especially ethylenic unsaturation, each monomer being capable of homopolymerizing (in contrast to polycondensates).

Radical-type polymers can preferably be vinylic polymers or copolymers, especially acrylic polymers.

Vinylic polymers can preferably result from the polymerization of monomers containing ethylenic unsaturation having at least one acid group and/or esters of these acidic monomers and/or amides of these acidic monomers.

Anionic radical polymers, i.e. monomers having at least one monomer containing an acidic group, are preferably used.

α,β-ethylenically unsaturated carboxylic acids such as acrylic acid, methacrylic acid, crotonic acid, maleic acid, itaconic acid and 2-acrylamido-2-methylpropanesulphonic acid can preferably be used as monomers bearing an acidic group. (Meth)acrylic acid and crotonic acid are more preferably used, and even more preferably (meth)acrylic acid.

The acidic monomer esters are advantageously selected from (meth)acrylic acid esters (also known as (meth) acrylates), especially alkyl (meth)acrylates, in particular of $C_1$–$C_{20}$ alkyl, preferably $C_1$–$C_8$ alkyl, aryl (meth)acrylates, in particular of $C_6$–$C_{10}$ aryl, and hydroxyalkyl (meth) acrylates, in particular of $C_2$–$C_6$ hydroxyalkyl.

Among the alkyl (meth)acrylates, mention may be made of methyl methacrylate, ethyl methacrylate, butyl methacrylate, isobutyl methacrylate, 2-ethylhexyl methacrylate and lauryl methacrylate.

Among the hydroxyalkyl (meth)acrylates, mention may be made of hydroxyethyl acrylate, 2-hydroxypropyl acrylate, hydroxyethyl methacrylate and 2-hydroxypropyl methacrylate.

Among the aryl (meth)acrylates, mention may be made of benzyl acrylate and phenyl acrylate.

The meth(acrylic) acid esters which are particularly preferred are the alkyl (meth)acrylates.

According to the present invention, the alkyl group of the esters can either be fluorinated or perfluorinated, i.e. some or all of the hydrogen atoms in the alkyl group are substituted with fluorine atoms.

As amides of acidic monomers, mention may be made, for example, of (meth)acrylamides, and especially N-alkyl (meth)acrylamides, in particular of $C_2$–$C_{12}$ alkyl. Among the N-alkyl (meth)acrylamides, mention may be made of N-ethyl acrylamide, N-t-butyl acrylamide and N-t-octyl acrylamide.

The vinylic polymers can also result from the homopolymerization or copolymerization of monomers selected from vinyl esters and styrene monomers. In particular, these monomers can be polymerized with acidic monomers and/or their esters and/or their amides, such as those mentioned above.

As examples of vinyl esters, mention may be made of vinyl acetate, vinyl neodecanoate, vinyl pivalate, vinyl benzoate and vinyl t-butylbenzoate.

As styrene monomers, mention may be made of styrene and α-methylstyrene.

The list of monomers given is not limiting and it is possible to use any monomer known to those skilled in the art in categories of acrylic and vinylic monomers.

According to the invention, a copolymer selected from (meth)acrylic acid/(meth)acrylate, (meth)acrylic acid/(meth) acrylate/styrene, (meth)acrylic acid/styrene, (meth)acrylic acid/α-methylstyrene copolymers and (meth)acrylate copolymers are preferably used as film-forming polymer. More preferably, a copolymer derived from the copolymerization of $C_1$–$C_8$ alkyl methacrylate monomers, optionally combined with acrylic acid, with styrene and with α-methylstyrene, is used.

When the polymer used according to the invention comprises monomers bearing a salifiable group (for example a carboxylic acid group), it can be neutralized, totally or partly, using a neutralizing agent (in this instance a base for neutralizing the acid group) which is well known to those skilled in the art. The neutralization can, in addition, assist the dispersing, in particular in water, of the polymer, or even stabilize the said dispersion.

Mention may also be made of the polymers resulting from the radical polymerization of one or more radical monomers inside and/or partially at the surface of pre-existing particles of at least one polymer selected from the group consisting of polyurethanes, polyureas, polyesters, polyester amides and/or alkyds. These polymers are generally known as hybrid polymers.

Advantageously, the radical film-forming polymer of the polymer system is present in the composition according to the invention either in solubilized (dissolved) form or in dispersed form, i.e. in the form of a dispersion of particles, in particular in a cosmetically or dermatologically acceptable medium. Preferably, the radical film-forming polymer is present in the form of an aqueous dispersion of particles of the polymer.

The aqueous dispersion comprising one or more film-forming polymers can be prepared by a person skilled in the art on the basis of his or her general knowledge. The solids content of the aqueous dispersions according to the present invention can preferably range from about 5 to about 60% by weight, and more preferably from 30 to 40%, relative to the total weight of the dispersion.

The size of the polymer particles in aqueous dispersion can preferably range from 10 to 500 nm, more preferably from 20 to 150 nm.

Advantageously, the hardness of the film obtained after applying the composition according to the invention to the support to be treated can have a hardness preferably of less than or equal to about 35, and more preferably less than or equal to about 20. In an even more preferred manner, the hardness of the film is greater than 1, and in particular greater than about 5.

Preferably, a film having a hardness preferably ranging from about 10 to 20, and more preferably from 13 to 18, gives in particular very good results of staying power of the film on the supports defined above, and in particular on the lips of the face. The hardness of the film is measured according to the conditions described before the examples.

The glass transition temperature (Tg) of the polymer system (or the film formed therefrom) according to the invention is advantageously less than or equal to about 0° C., more preferably less than or equal to about –10° C., even more preferably less than or equal to about –20° C. and still more preferably less than or equal to about –30° C.

The minimum film-forming temperature (MFT) of the polymer system according to the invention is advantageously less than or equal to about 12° C., more preferably less than or equal to about 8° C., even more preferably less than or equal to 5° C. and still more preferably less than or equal to 2° C.

Polymer systems which are particularly preferred are those having the following characteristics:

Tg ranging from −50° C. to −15° C.; MFT less than or equal to 5° C.; hardness of less than or equal to 25;

Tg ranging from −50° C. to −30° C.; MFT ranging from −5° C. to 5° C.; hardness ranging from 10 to 20, preferably 13 to 18;

Tg ranging from 5°C. to 10° C.; MFT ranging from 2° C. to 8° C.; hardness ranging from 3 to 10.

The application of a composition comprising such a polymer system to the lips leaves a film which has very good staying power on the lips. The film closely follows the movement of the lips without becoming detached or cracking.

According to a first embodiment of the composition according to the invention, the polymer system comprises solely at least one radical film-forming polymer having the characteristics as described above.

When the radical film-forming polymer does not make it possible to obtain only a film having the characteristics mentioned above, it is possible to add a compound whose function is to modify the properties of the film-forming polymer in order to obtain the desired polymer system. Thus, according to a second embodiment of the composition according to the invention, at least one auxiliary film-forming agent which allows a film having the characteristics as described above to be obtained can be added to the radical film-forming polymer. The auxiliary film-forming agent makes it possible in particular to obtain a soft, flexible film which follows the movement of the support on which the film is applied, in particular on the lips. In this case, the polymer system comprises a mixture of one or more radical film-forming polymers and at least one auxiliary film-forming agent.

Such an auxiliary film-forming agent can be selected from any compound known to those skilled in the art as being capable of fulfilling the desired function, and can be selected in particular from plasticizers. In addition, when the polymer system according to the invention comprises at least one aqueous dispersion of particles of film-forming polymer, the auxiliary film-forming agent can also be selected from coalescence agents. This auxiliary agent can be water-soluble or water-insoluble and can optionally be in the form of an aqueous dispersion.

In particular, mention may be made, alone or as a mixture, of common plasticizers or coalescence agents such as:

glycols and derivatives thereof such as diethylene glycol ethyl ether, diethylene glycol methyl ether, diethylene glycol butyl ether or diethylene glycol hexyl ether, ethylene glycol ethyl ether, ethylene glycol butyl ether or ethylene glycol hexyl ether;

glycerol esters, propylene glycol derivatives and in particular propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether and propylene glycol butyl ether, acid esters, in particular carboxylic acid esters, such as citrates, phthalates, adipates, carbonates, tartrates, phosphates and sebacates, oxyethylenated derivatives such as oxyethylenated oils, in particular plant oils such as castor oil; silicone oils, water-soluble polymers (or films formed therefrom) having a low glass transition temperature, of preferably less than 25° C., more preferably less than 15° C.

The amount of auxiliary film-forming agent can be selected by a person skilled in the art on the basis of his or her general knowledge, so as to obtain a polymer system leading to a film which has the desired mechanical properties, while the composition at the same time retains acceptable cosmetic properties.

When the film-forming polymer of the polymer system is an aqueous dispersion of 100% acrylic polymer, i.e. a polymer containing only monomers derived from (meth) acrylic acid (which includes the esters and amides) and containing no other monomers of styrene or vinyl ester type, the composition according to the invention is formulated with glycerol as plasticizer in a weight ratio of glycerol/solids in the acrylic polymer dispersion equal to about 4.17%.

The composition can preferably comprise from 1 to 60% by weight, more preferably from 5 to 40% by weight, of film-forming polymer solids relative to the total weight of the composition.

In order to carry out the present invention, it is thus necessary for the polymer system to allow a film to be obtained on the support on which it is deposited.

Moreover, in a preferred embodiment, the polymer system can be selected so as to make it possible to obtain a film having a Young's modulus of preferably less than about 200 MPa, more preferably less than about 100 MPa and even more preferably less than 85 MPa; advantageously, the Young's modulus is greater than 1 MPa, and/or an elongation preferably greater than about 200% and more preferably greater than 300%.

The methods for measuring the elongation and the Young's modulus (modulus of elasticity) are described before the examples.

The composition can also comprise at least one water-soluble dye and/or at least one pigment, which are used in the usual manner in the field of cosmetics and make-up. The term pigments should be understood to mean white or colored, inorganic or organic particles which are insoluble in the medium, intended to color and/or opacify the composition.

The pigments may be present in the composition in a proportion preferably ranging from 0 to 20% of the weight of the final composition, and more preferably in a proportion ranging from 1 to 5%. They may be white or colored, inorganic and/or organic, of the usual size or of nanometric size. Among the inorganic pigments and nanopigments, mention may be made of titanium oxide, zirconium oxide and cerium oxide, as well as zinc oxide, iron oxide, chromium oxide and ferric blue. Among the organic pigments, mention may be made of carbon black and barium, strontium, calcium and aluminium lakes. Among the water-soluble dyes, mention may be made of dyes that are common in the field considered, such as the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll.

Any known additive such as thickeners, for example clays, gums, silicas, cellulose derivatives, a synthetic polymer such as an acrylic polymer or an associative polymer of polyurethane type; a natural gum such as xanthan gum; spreading agents; dispersing agents; preserving agents; antifoaming agents; wetting agents; UV screening agents; fragrances; fillers; cosmetic active agents; moisturizers; vitamins and derivatives thereof; biological materials and derivatives thereof, may also be added to the composition according to the invention.

Obviously, a person skilled in the art will take care to select this or these optional additives and/or the amount thereof such that the advantageous properties of the composition according to the invention are not, or are not substantially, adversely affected by the addition envisaged.

The composition according to the invention can be in fluid, gelled, semi-solid or soft paste form, or even in solid form such as a stick or pencil. In the case of a non-solid formulation, the composition according to the invention preferably has a viscosity ranging from 0.05 Pa.s to 20 Pa.s (50 cPs to 20,000 cPs), and in particular from 0.05 Pa.s to 10 Pa.s, measured at 25° C. using a Brookfield DVII apparatus, 4 LVT rotor, rotational speed of 100 rpm, container size of 2.3 cm in diameter and 4 cm in height, without using a spindle guard.

The composition can be applied in particular as a make-up product, especially as a lip composition, such as a lipstick, a foundation, a blusher, an eyeshadow or an eyeliner, or alternatively as a make-up product for the body of the temporary or semi-permanent tattoo type. An application in the field of care compositions, especially for lip care, antisun or self-tanning compositions, dermatological compositions or pharmaceutical compositions to be applied to the skin, semi-mucous membranes and/or mucous membranes can also be envisaged.

The invention is illustrated in greater detail in the examples which follow.

A/Measurement of the hardness

The hardness of the film was measured according to ASTM standard D-43-66, or NF-T standard 30-016 (October 1981), using a Persoz pendulum.

The film deposited on the support should have a thickness of about 300 microns before drying. After drying for 24 hours, at 30° C. and under a relative humidity of 50%, a film having a thickness of about 100 microns was obtained; its hardness was then measured at 30° C. and 50% relative humidity.

B/Measurement of the elongation

The elongation of the film obtained was measured according to the ASTM Standards, volume 06.01 D 2370-92 "Standard Test Method for Tensile Properties of Organic Coatings".

C/Measurement of the Young's modulus (or modulus of elasticity)

The Young's modulus (modulus of elasticity) was measured according to ASTM Standards, Volume 06.01 D 2370-92 "Standard Test Method for Tensile Properties of Organic Coatings".

The film deposited on the support should have a thickness of about 300 microns before drying. After drying for 7 days at 21° C. and under a relative humidity of 50%, a film having a thickness of about 100 microns was obtained.

The samples measured had a width of 5 mm and a thickness of 100 microns. The distance between the jaws was 25 mm. The draw speed was 1000 mm per minute.

EXAMPLE 1

COMPARATIVE

The staying power of films obtained with various aqueous dispersions of acrylic resins, to which were added 2% by weight of pigment relative to the total weight of the dispersion, was measured and compared. The behaviour of the film applied to the lips was observed visually.

The study was carried out with 4 polymers according to the invention (P1 to P4) and 3 polymers not forming part of the invention (P'a to P'c).

The following results were obtained:

| Polymer | Tg (° C.) | MFT (° C.) | Hardness | Result |
|---|---|---|---|---|
| P1 | −34 | 0 | 15.4 | does not crack |
| P2 | 8 | 5 | 6.8 | does not crack |
| P3 | 0 | 10 | 33 | does not crack |
| P4 | −23 | <0 | 19.8 | does not crack |
| P'a | 9 | <0 | 79 | cracks rapidly |
| P'b | 24 | 14 | 27.5 | cracks rapidly |
| P'c | — | 20 | 80.3 | cracks rapidly |

P1: NEOCRYL A-1070 acrylic from Zeneca
P2: DOW LATEX 432 acrylic styrene from Dow Chemical
P3: NEOCRYL BT-62 acrylic styrene from Zeneca
P4: NEOCRYL A-523 acrylic from Zeneca
P'a: NEOCRYL A-1052 acrylic from Zeneca
P'b: DOW LATEX 424 acrylic styrene from Dow Chemical
P'c: NEOCRYL BT-67 acrylic from Zeneca The results obtained show that only the polymers according to the invention, i.e. polymers having a Tg≦10° C., an MFT≦15° C. and a hardness≦50 have good staying power on the lips, the film being flexible, following the movement of the lips and being comfortable to wear. In addition, the film deposited on the lips did not transfer.

EXAMPLE 2

A fluid composition to be applied to the lips, having the following composition, was prepared:

| | |
|---|---|
| aqueous dispersion of acrylic/styrene polymer sold under the name DOW LATEX 432 by the company Dow Chemical | 25 g AM |
| aqueous dispersion of fluoro wax (MICRODISPERSION 411 from Micropowders) | 5 g AM |
| pigment | 2 g |
| glycerol | 1.25 g |
| water qs | 100 g |

This composition was applied to the lips and a flexible film which did not crack and which followed the movement of the lips without becoming detached was obtained. In addition, the film did not transfer.

EXAMPLE 3

A fluid lip composition having the following composition was prepared:

| | |
|---|---|
| aqueous dispersion of acrylic polymer (NEOCRYL A-523 from the company Zeneca) | 20 g AM |
| microdispersion of fluoro wax (MICRODISPERSION 411 from Micropowders) | 2.5 g AM |
| glycerol | 1.875 g |
| thickener | 0.5 g |
| pigment | 3 g |
| water qs | 100 g |

The composition spread easily on the lips and left a flexible film which did not crack, was comfortable to wear and did not transfer.

EXAMPLE 4

A fluid lip composition having the following composition was prepared:

| | |
|---|---|
| aqueous dispersion of acrylic/styrene polymer (NEOCRYL A-1052 from Zeneca) | 20 g AM |
| acetyl tributyl citrate | 2.5 g |
| pigment | 2 g |
| glycerol | 1.25 g |
| water qs | 100 g |

A composition which was easy to apply to the lips was obtained. The film obtained did not transfer and had good staying power: it did not crack and followed the movement of the lips.

We claim:

1. A composition for the skin, semi-mucous membranes and/or mucous membranes comprising at least one polymer system comprising at least one film-forming radical polymer, wherein said polymer system has a glass transition temperature no greater than 10° C., a minimum film-forming temperature no greater than 15° C., said polymeric system being present in an amount effective to obtain a flexible and continuous film upon application to the skin, semi-mucous membranes and/or mucous membranes, wherein said continuous film has a hardness of less than 50.

2. A composition according to claim 1, wherein said glass transition temperature is no greater than 0° C.

3. A composition according to claim 2, wherein said glass transition temperature is no greater than −10° C.

4. A composition according to claim 3, wherein said glass transition temperature is no greater than −20° C.

5. A composition according to claim 4, wherein said glass transition temperature is no greater than −30° C.

6. A composition according to claim 1, wherein said minimum film-forming temperature is no greater than 12° C.

7. A composition according to claim 6, wherein said minimum film-forming temperature is no greater than 8° C.

8. A composition according to claim 7, wherein said minimum film-forming temperature is no greater than 5° C.

9. A composition according to claim 8, wherein said minimum film-forming temperature is no greater than 2° C.

10. A composition according to claim 1, wherein said hardness is no greater than 35.

11. A composition according to claim 10, wherein said hardness is no greater than 20.

12. A composition according to claim 1, wherein said hardness is greater than 1 and less than 50.

13. A composition according to claim 12, wherein said hardness is greater than 5 and less than 50.

14. A composition according to claim 11, wherein said hardness ranges from 10 to 20.

15. A composition according to claim 14, wherein said hardness ranges from 13 to 18.

16. A composition according to claim 1, wherein said glass transition temperature ranges from −50° C. to −15° C., said minimum film-forming temperature is no greater than 5° C. and said hardness is no greater than 25.

17. A composition according to claim 1, wherein said glass transition temperature ranges from −50° C. to −30° C., said minimum film-forming temperature ranges from −5° C. to 5° C. and said hardness ranges from 10 to 20.

18. A composition according to claim 17, wherein said hardness ranges from 13 to 18.

19. A composition according to claim 1, wherein said glass transition temperature ranges from 5° C. to 10° C., said minimum film-forming temperature ranges from 2° C. to 8° C. and said hardness ranges from 3 to 10.

20. A composition according to claim 1, wherein said at least one film-forming radical polymer is a vinylic polymer.

21. A composition according to claim 1, wherein said at least one film-forming radical polymer results from polymerization of monomers selected from α,β-ethylenic unsaturated carboxylic acids, (meth)acrylates,(meth)acrylamides, vinyl esters and styrene monomers.

22. A composition according to claim 1, wherein said at least one film-forming radical polymer is selected from copolymers formed from (meth)acrylic acid/(meth)acrylate, (meth)acrylic acid/(meth)acrylate/styrene, (meth)acrylic acid/styrene, (meth)acrylic acid/α-methylstyrene copolymers and meth)acrylate copolymers.

23. A composition according to claim 1, wherein said at least one film-forming radical polymer is derived from the copolymerization of $C_1$–$C_8$ alkyl methacrylate monomers, optionally combined with acrylic acid, with styrene and with α-methylstyrene.

24. A cosmetic or dermatological composition comprising at least one polymer system comprising at least one film-forming radical polymer, wherein said polymer system has a glass transition temperature no greater than 10° C., a minimum film-forming temperature no greater than 15° C., said polymeric system being present in an amount effective to obtain a flexible and continuous film upon application to the skin, semi-mucous membranes and/or mucous membranes, wherein said continuous film has a hardness of less than 50.

25. A make-up product comprising at least one polymer system comprising at least one film-forming radical polymer, wherein said polymer system has a glass transition temperature no greater than 10° C., a minimum film-forming temperature no greater than 15° C., said polymeric system being present in an amount effective to obtain a flexible and continuous film upon application to the skin, semi-mucous membranes and/or mucous membranes, wherein said continuous film has a hardness of less than 50.

26. A lip composition, eyeliner, foundation, eyeshadow, blusher, or make-up product for the body comprising at least one polymer system comprising at least one film-forming radical polymer, wherein said polymer system has a glass transition temperature no greater than 10° C., a minimum film-forming temperature no greater than 15° C., said polymeric system being present in an amount effective to obtain a flexible and continuous film upon application to the skin, semi-mucous membranes and/or mucous membranes, wherein said continuous film has a hardness of less than 50.

27. A lip composition according to claim 26, wherein said lip composition is a lip lacquer or lip care composition.

28. A lip care composition, an anti-sun composition, or a self-tanning composition comprising at least one polymer system comprising at least one film-forming radical polymer, wherein said polymer system has a glass transition temperature no greater than 10° C., a minimum film-forming temperature no greater than 15° C., said polymeric system being present in an amount effective to obtain a flexible and continuous film upon application to the skin, semi-mucous membranes and/or mucous membranes, wherein said continuous film has a hardness of less than 50.

29. A composition according to claim 1, wherein said film has a Young's modulus of less than 200 MPa.

30. A composition according to claim 29, wherein said film has a Young's modulus of less than 100 MPa.

31. A composition according to claim 30, wherein said film has a Young's modulus of less than 85 MPa.

32. A composition according to claim 1, wherein said film has a Young's modulus greater than 1 Mpa and less than 200 MPa.

33. A composition according to claim 32, wherein said film has a Young's modulus greater than 5 Mpa and less than 200 MPa.

34. A composition according to claim 1, wherein said film has an elongation greater than 200%.

35. A composition according to claim 34, wherein said film has an elongation greater than 300%.

36. A composition according to claim 1, wherein said composition further comprises at least one additive.

37. A lipstick comprising at least one polymer system in an amount capable of forming a flexible and continuous film on the lips and of following the movements of said lips, wherein said polymer system comprises at least one film-forming radical polymer obtained from the copolymerization of $C_1$–$C_8$ alkyl methacrylate monomers, optionally combined with acrylic acid, styrene and α-methylstyrene.

38. A lipstick according to claim 37, wherein said $C_1$–$C_8$ alkyl methacrylate monomers are selected from alkyl (meth) acrylates.

39. A lipstick according to claim 38, wherein said alkyl (meth)acrylates are selected from $C_1$–$C_{20}$ alkyls.

40. A lipstick according to claim 39, wherein said alkyl (meth)acrylates are selected from $C_1$–$C_8$ alkyls.

41. A composition according to claim 1, wherein said composition is in the form of a fluid, a gel, a semi-solid, a soft paste, or a solid.

42. A process for making up a support comprising applying to said support an effective amount of at least one polymer system comprising at least one film-forming radical polymer, wherein said polymer system has a glass transition temperature no greater than 10° C., a minimum film-forming temperature no greater than 15° C., said polymeric system being present in an amount effective to obtain a flexible and continuous film upon application to said support, wherein said continuous film has a hardness of less than 50.

43. A process according to claim 42, wherein said support is selected from skin, semi-mucous membranes and mucous membranes.

44. A process for non-therapeutic treatment of a support comprising applying to said support an effective amount of at least one polymer system comprising at least one film-forming radical polymer, wherein said polymer system has a glass transition temperature no greater than 10° C., a minimum film-forming temperature no greater than 15° C., said polymeric system being present in an amount effective to obtain a flexible and continuous film upon application to said support, wherein said continuous film has a hardness of less than 50.

45. A process according to claim 44, wherein said support is selected from skin, semi-mucous membranes and mucous membranes.

46. A method of therapeutically treating the skin, semi-mucous membranes and/or mucous membranes comprising applying thereto an effective amount of at least one polymer system comprising at least one film-forming radical polymer, wherein said polymer system has a glass transition temperature no greater than 10° C., a minimum film-forming temperature no greater than 15° C., said polymeric system being present in an amount effective to obtain a flexible and continuous film upon application to the skin, semi-mucous membranes and/or mucous membranes, wherein said continuous film has a hardness of less than 50.

47. A method of reducing the transfer and/or migration of a composition to be applied to skin, semi-mucous membranes and/or mucous membranes, comprising incorporating in a composition at least one polymer system comprising at least one film-forming radical polymer, wherein said polymer system has a glass transition temperature no greater than 10° C., a minimum film-forming temperature no greater than 15° C., said polymeric system being present in an amount effective to obtain a flexible and continuous film upon application to the skin, semi-mucous membranes and/or mucous membranes, wherein said continuous film has a hardness of less than 50.

48. A lipstick according to claim 37, wherein said polymer system has a glass transition temperature of less than or equal to 10° C.

49. A lipstick according to claim 48, wherein said polymer system has a glass transition temperature ofless than or equal to 0° C.

50. A lipstick according to claim 37, wherein said film has a hardness of less than or equal to 50.

51. A lipstick according to claim 50, wherein said film has a hardness of less than or equal to 35.

52. A lipstick according to claim 37, wherein said polymer system has a minimum film-forming temperature of less than or equal to 15° C.

53. A lipstick according to claim 52, wherein said polymer system has a minimum film-forming temperature of less than or equal to 8° C.

54. A composition according to claim 1, wherein said film-forming radical polymer is dissolved.

55. A composition according to claim 1, wherein said film-forming radical polymer is dispersed.

56. A composition according to claim 55, wherein said film-forming radical polymer is in the form of particles in aqueous dispersion.

57. A composition according to claim 56, wherein said particles of said aqueous dispersion have a size ranging from 10 to 500 nm.

58. A composition according to claim 57, wherein said particles of said aqueous dispersion have a size ranging from 20 to 150 nm.

59. A composition according to claim 1, wherein said polymer system comprises solely one or more film-forming radical polymer(s).

60. A composition according to claim 1, wherein said polymer system further comprises at least one auxiliary film-forming agent.

61. A composition according to claim 60, wherein said auxiliary film-forming agent is a plasticizer.

62. A composition according to claim 60, wherein said auxiliary film-forming agent is a coalescence agent.

63. A composition according to claim 1, wherein said at least one film-forming radical polymer is present in an amount ranging from 1 to 60% by weight of solids relative to the total weight of the composition.

64. A composition according to claim 63, wherein said at least one film-forming radical polymer is present in an amount rangingfrom 5 to 40% by weight of solids relative to the total weight of the composition.

* * * * *